(12) United States Patent
Palermo

(10) Patent No.: US 6,481,219 B2
(45) Date of Patent: Nov. 19, 2002

(54) DISINFECTION SYSTEM AND METHOD OF USING SAME

(75) Inventor: Henry William Palermo, Burbank, CA (US)

(73) Assignee: Sakura Finetek U.S.A., Inc., Torrance, CA (US)

( * ) Notice: Subject to any disclaimer, the term of this patent is extended or adjusted under 35 U.S.C. 154(b) by 0 days.

(21) Appl. No.: 09/822,150

(22) Filed: Mar. 30, 2001

(65) Prior Publication Data

US 2002/0139124 A1 Oct. 3, 2002

(51) Int. Cl.[7] .................................................. F25B 19/00
(52) U.S. Cl. ............................................................ 62/51.1
(58) Field of Search ..................................... 62/51.1, 78

(56) References Cited

U.S. PATENT DOCUMENTS

| | | | |
|---|---|---|---|
| 4,854,128 A | * 8/1989 | Zeamer | 62/50.1 |
| 5,156,019 A | 10/1992 | McCormick | |
| 5,255,585 A | 10/1993 | Gordon | |
| 5,452,584 A | 9/1995 | Diggs | |
| 5,520,893 A | 5/1996 | Kasting, Jr. et al. | |
| 5,624,734 A | 4/1997 | Rees et al. | |
| 5,628,197 A | 5/1997 | Rada | |
| 5,865,081 A | 2/1999 | Myers | |
| 5,914,089 A | 6/1999 | Murakami et al. | |
| 5,960,640 A | 10/1999 | Teppke | |
| 5,974,811 A | * 11/1999 | Heid et al. | 62/78 |
| 5,988,029 A | 11/1999 | Rotterman et al. | |
| 6,231,676 B1 | * 5/2001 | Rudd et al. | 134/1 |
| 6,280,633 B1 | * 8/2001 | Conrad et al. | 210/739 |

* cited by examiner

Primary Examiner—William C. Doerrler
Assistant Examiner—Malik N. Drake
(74) Attorney, Agent, or Firm—Luce, Forward, Hamilton & Scripps LLP

(57) ABSTRACT

An apparatus and method for disinfecting a microtome and cryostat is provided. The cryostat comprises a chamber, a pump communicating with the chamber, an ozone generator and an ozone destroyer. A microtome is located in the chamber. Oxygen molecules in ambient air are converted to ozone that is injected into the cryostat chamber, disinfecting the chamber and the microtome. After disinfection, the air and ozone present in the chamber is directed to an ozone destroying unit that eliminates any remaining ozone. This eliminates the risk of ozone exposure to nearby operators and minimizes damage to the cryostat and microtome from extended ozone contact.

38 Claims, 7 Drawing Sheets

DISINFECTION SYSTEM AND METHOD OF USING SAME

FIELD OF THE INVENTION

The present invention generally relates to disinfection of medical instruments using ozone.

BACKGROUND OF THE INVENTION

Analysis of biological material is often performed by thinly slicing the material so that it can be viewed under a microscope. Various devices are employed for making the thin tissue samples, such as razor blades and microtome instruments. The material can be prepared for cutting by embedding the it in a supportive matrix, such as a paraffin based matrix, and then freezing the matrix and embedded biological material. The frozen matrix and embedded material cut, such as by the microtome to produce thin sections, which can then be stained and placed on a microscope slide for subsequent viewing.

A cryostat is an apparatus that provides a low-temperature environment and, accordingly, is widely used in the health care industry to freeze biological samples for later analysis. Microtomes and cryostats have been combined, producing an apparatus that can maintain biological samples in a frozen state, while thinly slicing them for examination.

During use, a cryostat and microtome may process biological samples from many different sources. To prevent contamination from sample to sample, it is desirable to periodically clean and disinfect the microtome and/or cryostat chamber. Similarly, the microtome and cryostat chamber must be cleaned and disinfected to prevent contamination from naturally occurring viruses, bacteria, and spores. Furthermore, disinfection of the microtome and cryostat chamber reduces the infection risk to operators from the biological samples.

Ozone is a known disinfecting agent that is effective in killing bacteria that are otherwise resistant to antibiotics. Ozone ($O_3$) in a gaseous state can diffluse through an entire enclosure, disinfecting all surfaces within the space. However, ozone also tends to be chemically unstable, readily converting to oxygen ($O_2$). Furthermore, ozone is toxic to humans when inhaled in high concentrations. These disadvantages have limited the use of ozone as a disinfecting agent in certain applications.

To overcome the problems with using ozone to disinfect medical equipment, it is known to employ water containing dissolved ozone. One method disinfects medical equipment by soaking the equipment in water containing sufficiently high amounts of dissolved ozone. Another method circulates water containing dissolved ozone around medical equipment. However, water containing dissolved ozone cannot be used to disinfect a cryostat chamber and microtome because the low temperatures typically present in the cryostat can freeze the water. Warming the cryostat chamber and microtome for disinfection with ozone-containing water is unfeasible because of the extensive processing time required to warm sterilize, and re-cool the cryostat.

Accordingly, there is a need for an apparatus and method to employ ozone to disinfect a cryostat and an associated microtome.

SUMMARY OF THE INVENTION

The present invention alleviates to a great extent the disadvantages of the known apparatus and methods for disinfecting medical instruments such as microtomes and cryostats by providing an enclosure that employs ozone for disinfection. In a preferred embodiment, the present invention includes a cryostat with an enclosable chamber, a pump, an ozone generator generating ozone, and an ozone destroyer.

In one embodiment, the pump creates a slight vacuum to verify the integrity of the cryostat chamber. The ozone generator creates ozone from oxygen present in the cryostat chamber air. The ozone diffuses through the cryostat chamber, disinfecting the microtome and chamber. After decontamination, the pump flushes the air/ozone from the cryostat chamber to the ozone destroyer. The ozone destroyer eliminates any remaining ozone.

In another embodiment of the present invention, a three-way valve directs the output of the pump. By regulating the output of the pump, the three-way valve controls the process of decontamination. In another embodiment of the invention, a second pump is employed. Ozone is created outside the cryostat chamber and the second pump directs the ozone into the cryostat chamber or to the ozone destroyer. If the first pump fails, the second pump directs the air/ozone to the ozone destroyer. In this way, any ozone in the cryostat chamber is eliminated, even if the first pump fails.

In another embodiment of the invention, a secondary power source is provided to supply backup power in case of a primary power failure. In yet another embodiment of the invention, a safety mechanism locks the cryostat chamber to prevent opening of the chamber during ozone decontamination.

These and other features and advantages of the present invention will be appreciated from review of the following detailed description of the invention, along with the accompanying figures in which like reference numerals refer to like parts throughout.

DETAILED DESCRIPTION OF THE INVENTION

Figure 1:
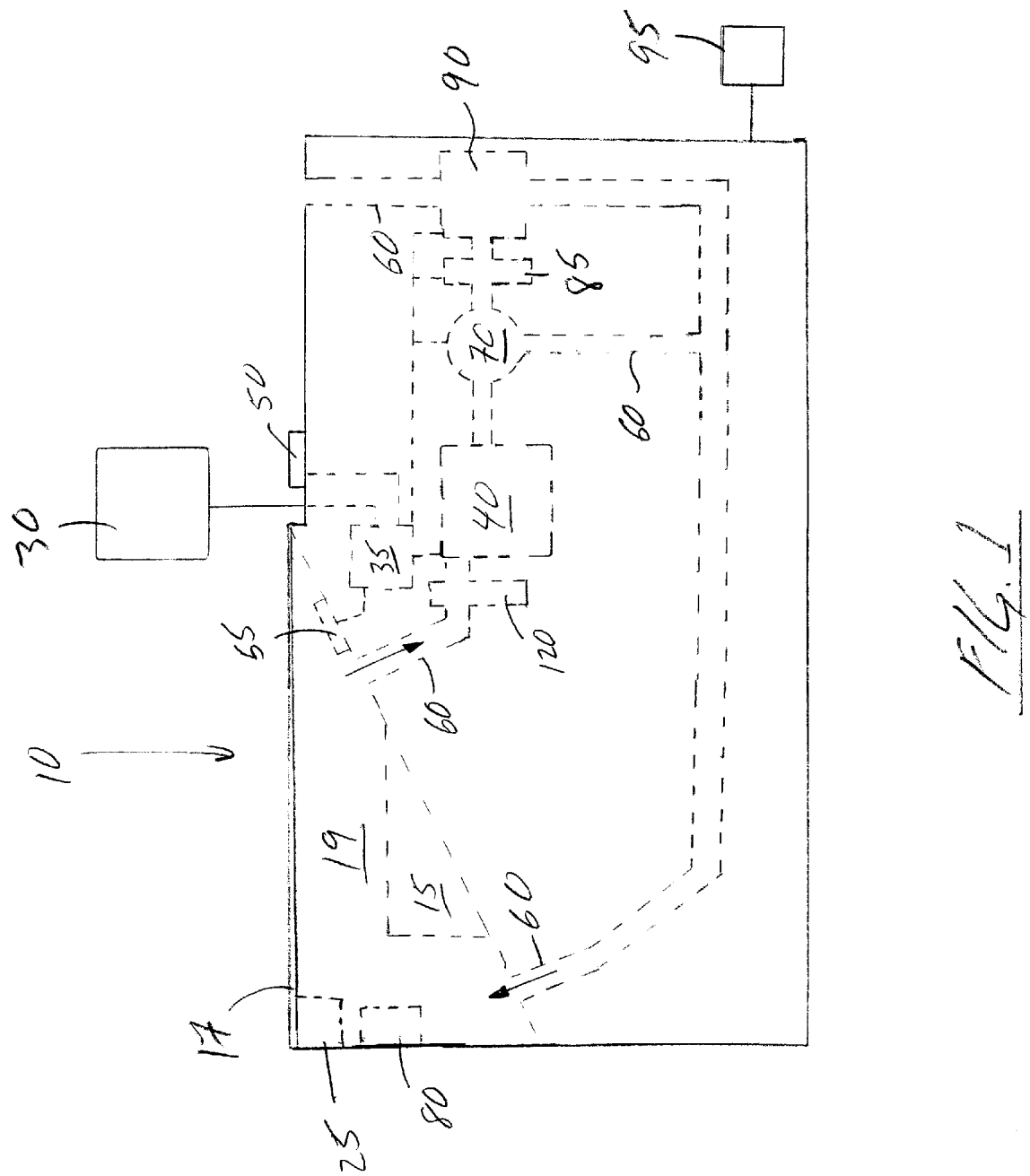
FIG. 1 is a side elevation view of one embodiment of the present invention.

In the following paragraphs, the present invention will be described in detail by way of example with reference to the attached drawings. Throughout this description, the preferred embodiment and examples shown should be considered as exemplars, rather than as limitations on the present invention. As used herein, "the present invention" refers to any one of the embodiments of the invention described herein.

The present invention alleviates to a great extent the disadvantages of known apparatus and methods for disinfecting a cryostat by providing a cryostat that disinfects itself with ozone. In general, the present invention includes a cryostat with a chamber, a pump, an ozone generator, and an ozone destroyer. The ozone generator and a microtome are located in the cryostat chamber. The ozone generator creates ozone from oxygen ($O_2$) present in the cryostat chamber. The ozone diffuses throughout the cryostat chamber, decontaminating all surfaces within the chamber. After decontamination, the pump directs the air/ozone in the cryostat chamber to the ozone destroyer. The ozone destroyer eliminates the ozone and converts it back to oxygen.

Alternatively, the pump can be employed to circulate the ozone within the cryostat chamber. Also, the ozone generator may be located outside the cryostat chamber, with the pump directing the ozone into the cryostat chamber.

One aspect of the present invention is a safety feature in the form of two pumps. If the first pump fails, the second pump directs all the air/ozone in the cryostat chamber to the ozone destroyer. In this way, any ozone in the cryostat chamber is eliminated. This design helps avoid risk of damage to the cryostat chamber and microtome from extended ozone contact. Furthermore, the fail-safe feature provided by the second pump reduces the risk of human contact with ozone.

The present invention also provides a method for decontaminating a cryostat and microtome that includes the steps of: 1) introducing ozone into the cryostat chamber, or generating ozone within the cryostat chamber; 2) removing the ozone remaining in the cryostat chamber after decontamination; and 3) eliminating any remaining ozone. In an alternative embodiment, the method also includes locking and sealing the cryostat chamber prior to the step of introducing of the ozone into the cryostat chamber.

Referring to FIGS. 1–4, the present invention comprises a cryostat 10 having a chamber 19 enclosed by a viewing window 17 that is secured by window lock 25. Located within the cryostat chamber 19 is microtome 15. The cryostat 10 also includes an operator interface 30 that communicates with controller 35. Preferably, the controller 35 is a general computing device that can be programmed to perform various functions related to the operation of the cryostat 10. The controller 35 communicates with window lock 25, pump 40, ozone generator 80, ozone destroyer 90, and other devices comprising the cryostat 10 to operate the cryostat 10 as directed through the operator interface 30.

The cryostat 10 generates temperatures that range from about −50° C. to about +25° C. in the cryostat chamber 19. Located within the cryostat chamber 19 is the microtome 15. The microtome produces very thin slices of biological material for medical analysis. The cryostat chamber 19 is kept at a low temperature to maintain the biological samples, and to slow the growth of any spores, viruses or bacteria that may be present. To minimize the risk of contamination from the bacteria and other microorganisms, the microtome 15 and cryostat chamber 19 should be decontaminated frequently.

One aspect of the present invention is the use of ozone to decontaminate the cryostat chamber 19 and microtome 15. Ozone ($O_3$) is an unstable molecule that is generally produced by exposing oxygen ($O_2$) to ultraviolet radiation. Ozone is a very powerful decontaminant that can quickly destroy bacteria and other microorganisms, but ozone may also produce harmful health effects in humans. Therefore, another aspect of the present invention are several fail-safe devices and apparatus to minimize any ozone exposure to operators and technicians.

Figure 3:
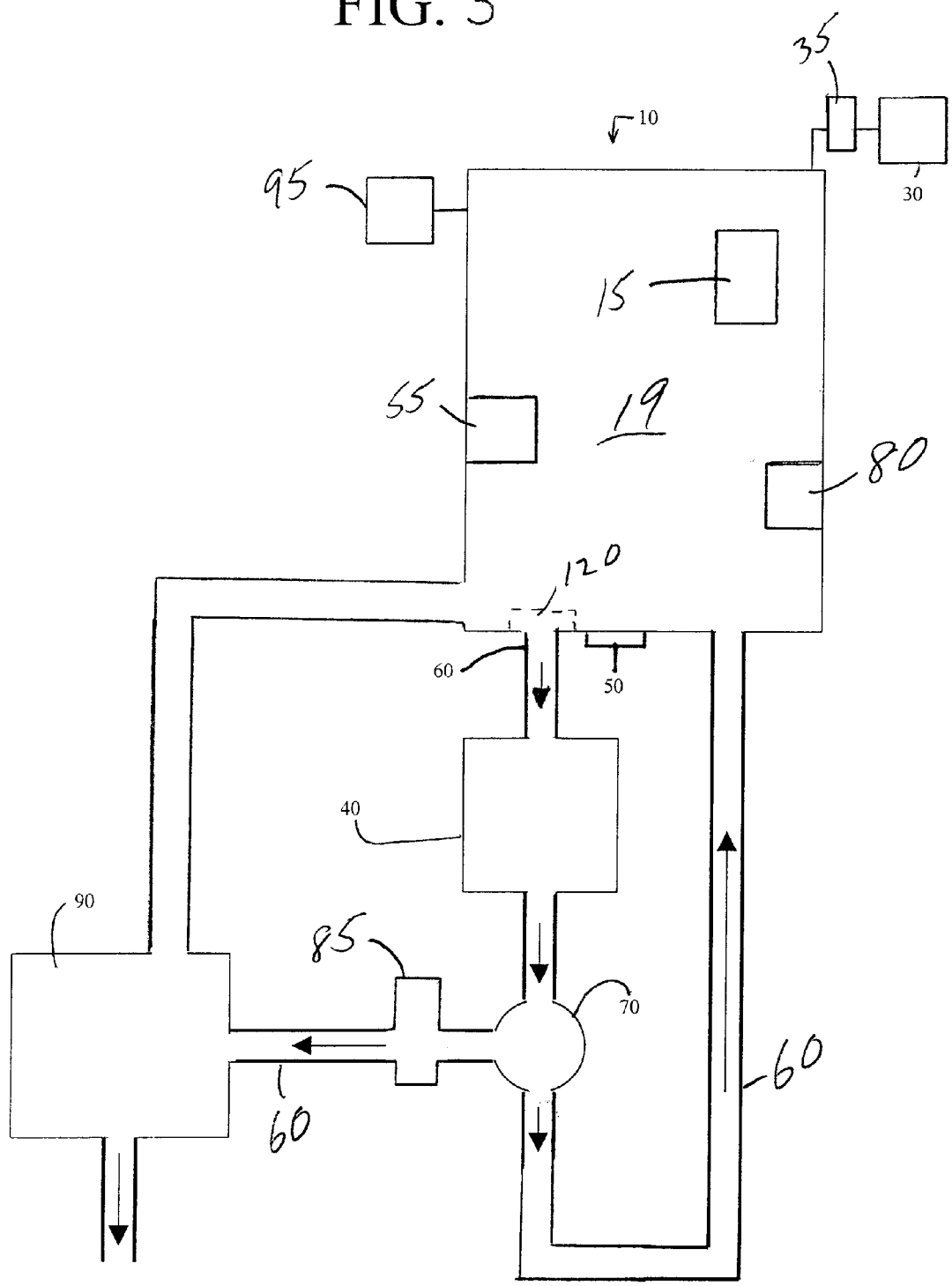
FIG. 3 is a schematic diagram of the embodiment illustrated in FIG. 1.

Referring to FIGS. 1 and 3, the cryostat includes an ozone generator 80 that produces ozone ($O_3$) from oxygen ($O_2$). In this embodiment, the ozone generator 80 may be located within the cryostat chamber 19. In other embodiments, the ozone generator 80 may be located within the cryostat 10, but outside the cryostat chamber 19, or the ozone generator 80 may be located outside the cryostat 10.

The ozone generator 80 may employ either a corona discharge device or an ultraviolet (UV) lamp to generate ultraviolet radiation. Either device creates ozone from oxygen present in the cryostat chamber 19 by splitting oxygen molecules ($O_2$) to form two unstable oxygen atoms (O) that subsequently combine with other oxygen molecules to form ozone ($O_3$). One embodiment of the present invention employs a UV lamp ozone generator 80 that also includes a UV lamp guard (not illustrated) that protects the lamp from contact by operators. A safety feature included in the cryostat 10 is that when the viewing window 17 is open, the UV lamp will not operate, thereby preventing UV expose to an operator. In one embodiment, the ozone generator 80 may be constructed to operate maintenance-free for at least 1,000 hours in temperatures ranging between −50° C. to +25° C. Other types of ozone generators 80 may be employed in the present invention, including corona discharge devices and other devices structured to generate ultraviolet radiation.

Figure 2:
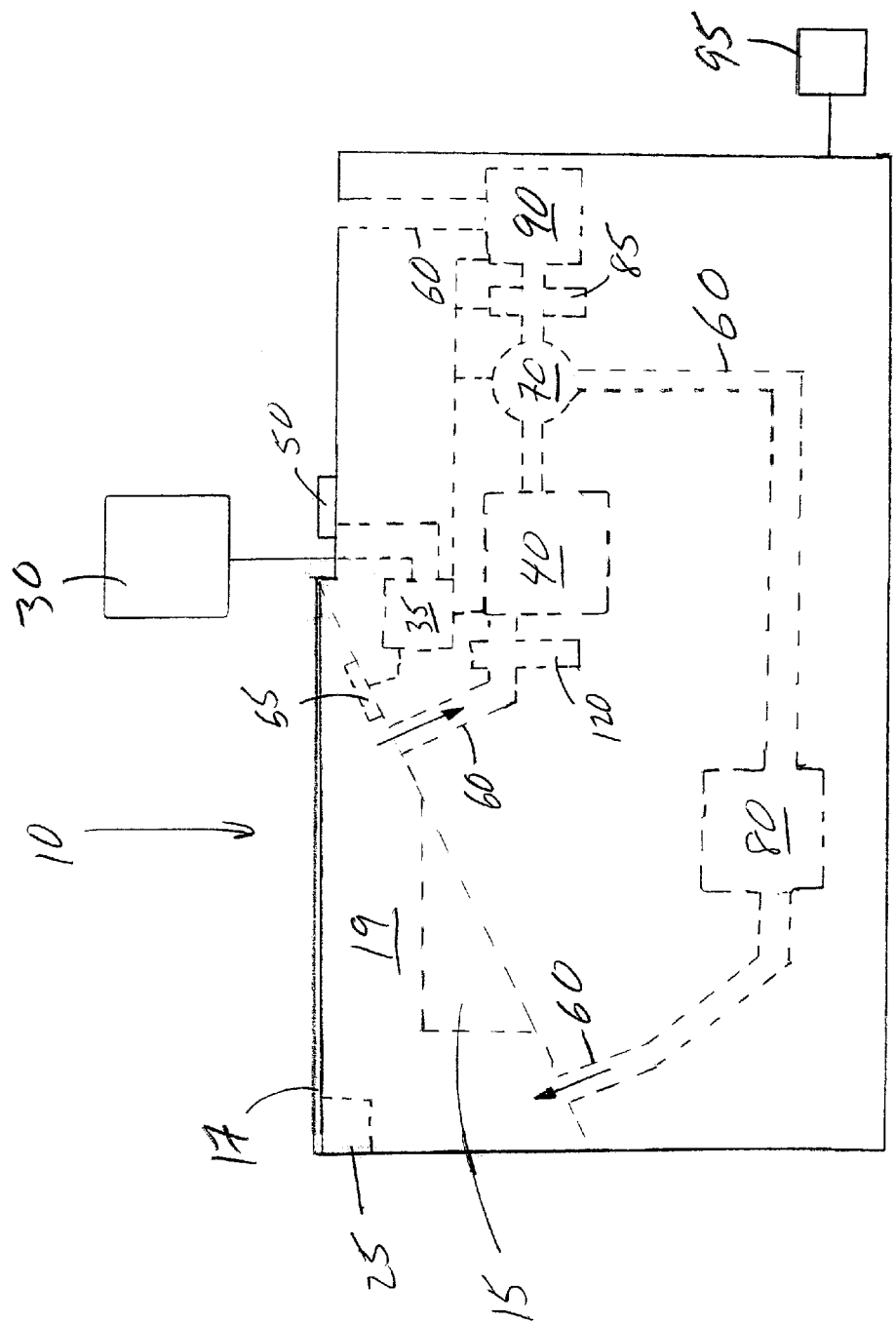
FIG. 2 is a side elevation view of another embodiment of the present invention
Figure 4:
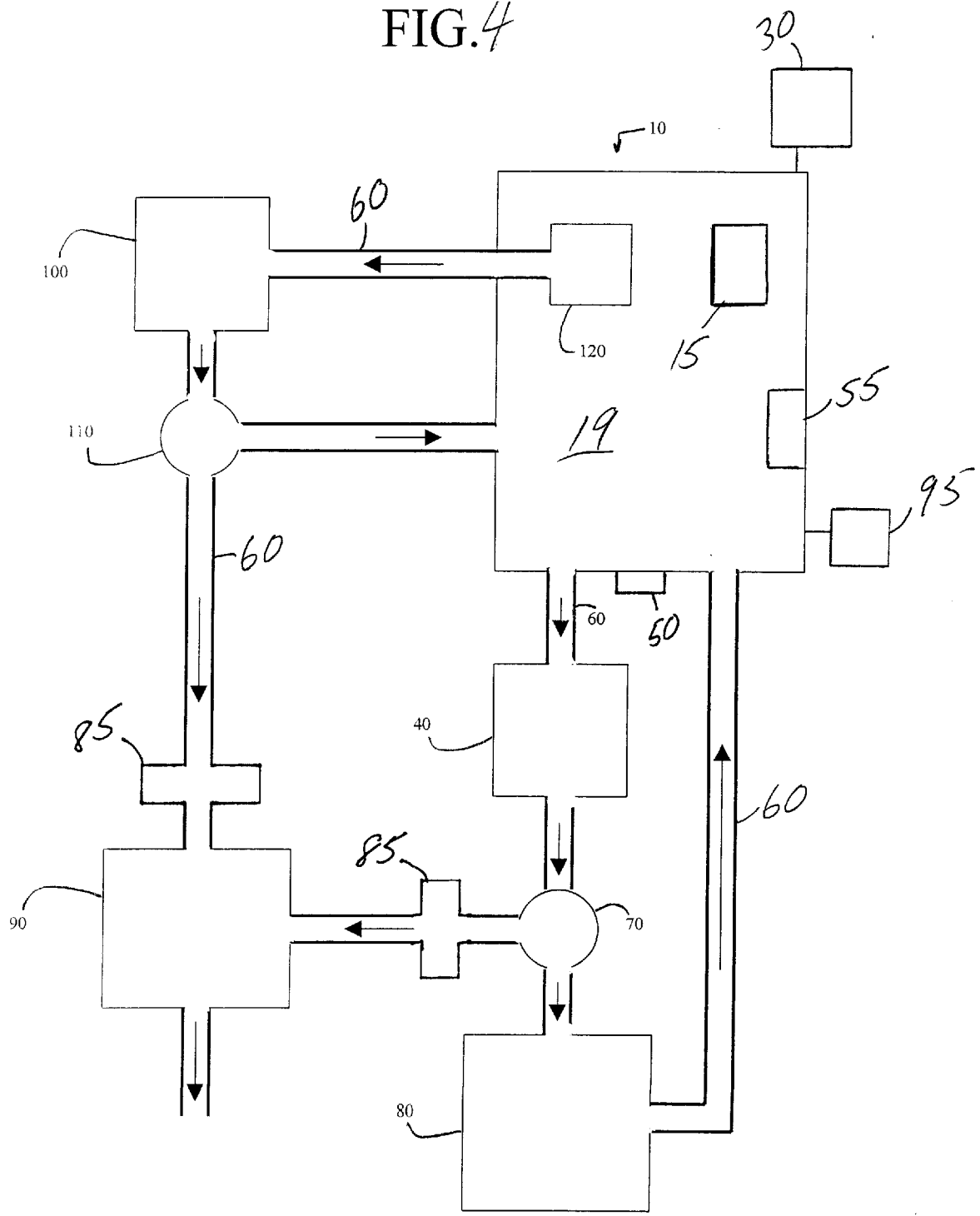
FIG. 4 is a schematic diagram of another embodiment of the present invention.

Referring to FIGS. 2 and 4, an alternative embodiment of the present invention is illustrated. This embodiment locates the ozone generator 80 outside the cryostat chamber 19. At least one pump 40 and one valve 70 direct air to the ozone generator 80. When generating ozone, controller 35 directs valve 70 to output air received from the cryostat chamber 19 through pump 40 to the ozone generator 80. When destroying ozone, controller 35 directs valve 70 to output air/ozone received from the cryostat chamber 19 through pump 40 to the ozone destroyer 90. An optional filter 120 may be attached to pipe 60 that will filter the cryostat chamber 19 air before it contacts pump 40. Preferably, the filter 120 is ozone resistant, and may be a single-stage or a two-stage filter design. A two-stage filter 120 may also include chemical compounds such as carbon to remove contaminants from the cryostat chamber 19 air.

Referring to FIG. 4, an alternative embodiment of the present invention is illustrated, which employs a second pump 100 and a second valve 110. During operation of the microtome 15, the second pump 100 circulates air in the cryostat chamber 19. An optional filter 120 can be attached to pipe 60 that will filter the cryostat air before it is re-circulated. However, in case the first pump 40 fails, second valve 110 is automatically directed by controller 35 to direct air received from the cryostat chamber 19 to the ozone destroyer 90. In this way, any ozone in the cryostat chamber 19 is eliminated. This fail-safe feature avoids damage to the cryostat chamber 19 and microtome 15 from extended ozone contact. In an alternative embodiment, an ozone sensor in sensor packet 55 may be used to monitor the concentration of ozone inside the cryostat chamber 19. Output from the ozone sensor may be monitored by controller 35 before release of the viewing window lock 25. This additional safety feature minimizes operator exposure to ozone.

An airflow sensor included within a sensor packet 55 may also be used to measure airflow from the first pump 40. If the airflow drops below a predetermined amount, the operator interface 30 will indicate a system failure. If this occurs, the second pump 110 will evacuate the cryostat chamber 19 and valve 110 will direct the air/ozone to the ozone destroyer 90. Preferably, the valves 70 and 110 are three-way ball valves, but other types of valves, such as solenoid valves, and manual or automatic ball valves and solenoid valves, may be employed.

An alternative embodiment of the present invention may include a secondary power source 95, shown in FIGS. 1–4. In case of a main power failure during a decontamination cycle, the controller 35 will access the secondary power source 95. Preferably, the secondary power source 95 is sufficient to display an alarm at the operator interface 30 and operate at least one valve 70 and 110, and at least one pump 40 and 100 to destroy any ozone. For example, when the primary power source fails, and the controller 35 switches to the secondary power source 95, at least one of the first and second pumps, 40 and 100 are energized for a pre-determined time period, to evacuate air/ozone from the cryostat chamber 19. Only after the pre-determined time period has passed, does the cryostat viewing window 17 open, by releasing lock 25. If the secondary power source 95 fails before the pre-determined time period, the cryostat viewing window 17 remains locked. The secondary power source 95 may comprise a battery, but other types of power sources may also be employed, such as a fuel cell, a photovoltaic system, or other suitable power sources.

Referring to FIGS. 1–4, located downstream from both the first and second pumps 40 and 100, respectively, is ozone destroyer 90. The ozone destroyer 90 eliminates any ozone present in the air that the ozone destroyer 90 receives from the first or second pumps 40 and 100. Ozone destroyer 90 may be constructed from thermal devices that expose ozone to high temperatures, Noble-metal catalysts, manganese dioxide catalysts and activated carbon devices. Preferably, the ozone destroyer 90 is a CARULITE catalyst (CARULITE is a registered trademark of the Carus Corp. of Peru, Ill.). Preferably, the ozone concentration measured at the outlet of the ozone destroyer 90 will be less than 1 part per million. Another embodiment of the present invention may include a heater 85, that heats the air/ozone before it reaches the ozone destroyer 90. The ozone destroyer 90 operates more efficiently at elevated temperatures, and ozone deteriorates more rapidly at elevated temperatures.

Figure 5:
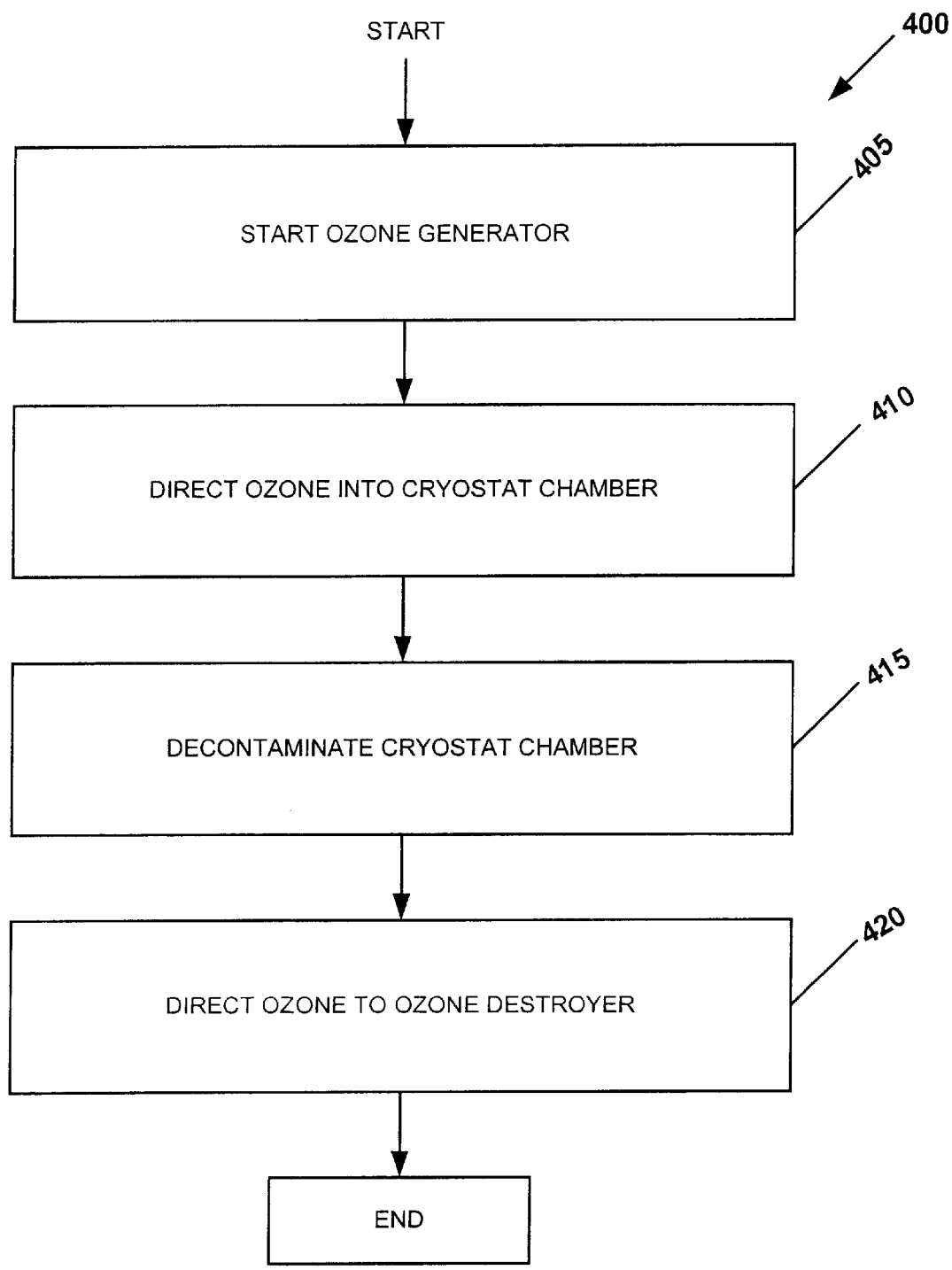
FIG. 5 is a flowchart illustrating one method of operating any one of the embodments illustrated in FIGS. 1–4.

Referring to FIG. 5, one method 400 of operating the present invention is illustrated. In step 405, the ozone generator is started and in step 410, the ozone generated by the ozone generator is directed into the cryostat chamber 19. In one embodiment, the ozone may be generated within the cryostat chamber 19, and the step of directing ozone into the cryostat chamber 19 may simply comprise activating the ozone generator. In another embodiment, the ozone may be generated outside the cryostat chamber 19, and the step of directing ozone into the cryostat chamber 19 may include pumping the ozone into the chamber 19.

In step 415, the ozone in the cryostat chamber 19 decontaminates the cryostat chamber eliminating any bacteria, viruses or spores. In step 420, pump 40 evacuates the air and ozone present in the cryostat chamber 19 and directs it to an ozone destroyer 90 that eliminates any remaining ozone. After all the ozone is destroyed, the decontamination cycle is complete. At least two operation cycles are available for decontamination. A long decontamination cycle may be performed during defrost of the cryostat chamber 19, or it may be performed at other times of cryostat 10 operation. All surfaces inside the cryostat chamber 19, including those covered with ice, will be decontaminated. Decontamination is defined as the elimination of about 99% of the bacteria, viruses and spores present before decontamination. The long cycle may last for approximately one hour. Alternatively, a short decontamination cycle can be initiated at anytime through the operator interface 30. All bacteria, viruses and most spores will be eliminated during a short decontamination cycle. The short cycle may last for about 15 to 30 minutes, and the cryostat 10 does not need to be defrosted before the start of a short cycle. At any time during either a long or short decontamination cycle, an operator will be able to abort the decontamination cycle through the operator interface 30. The ozone generator 80 will stop operation and ozone destruction will begin.

Figure 6:
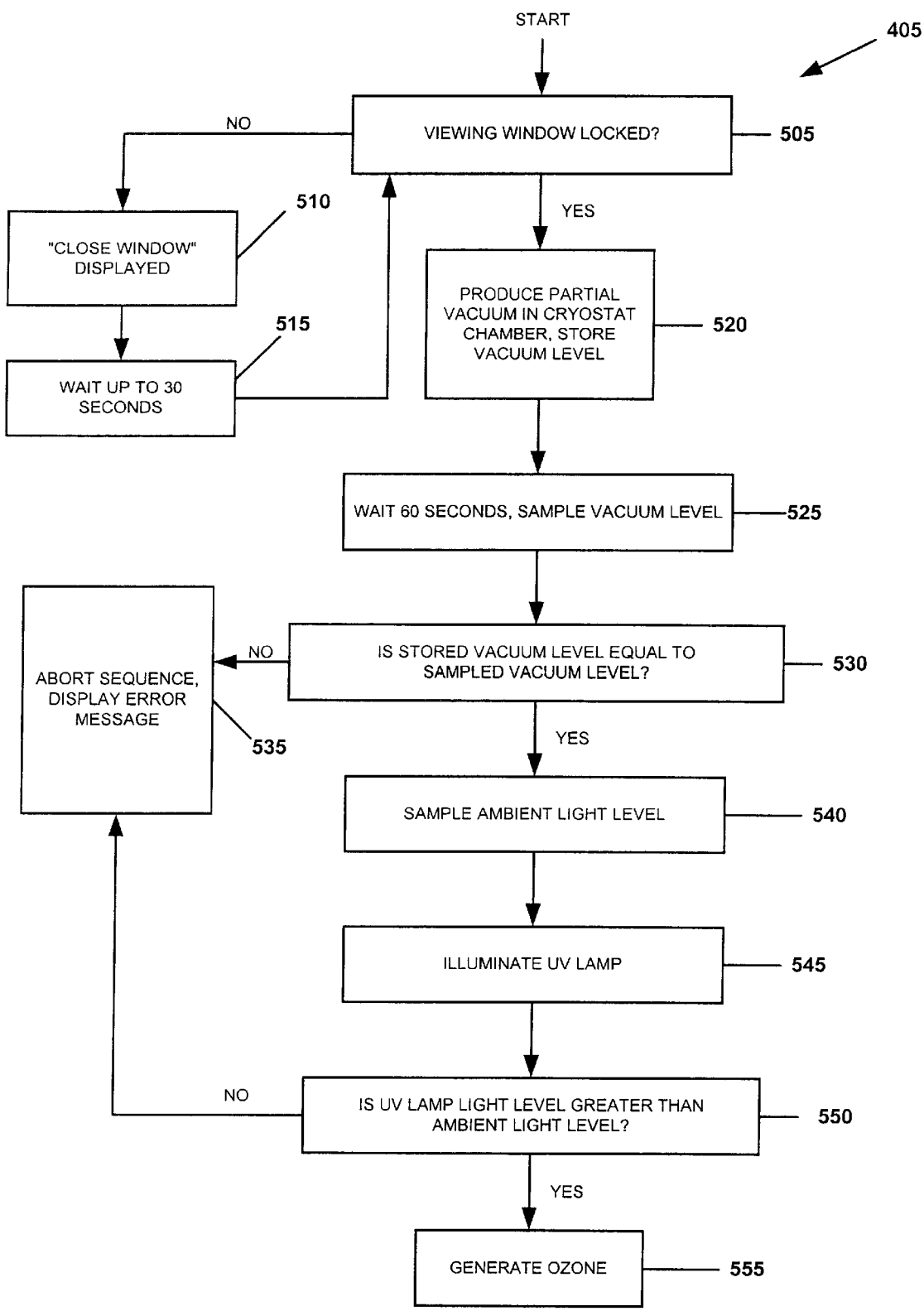
FIG. 6 is a flowchart illustrating one method of performing a method step shown in FIG. 5.

Operation of the cryostat 10 is substantially identical in both decontamination cycles, and will be described in detail with reference to FIG. 6, which illustrates a detailed flow-chart of method step 405, shown in FIG. 5. At the start of a decontamination sequence, the "$O_3$" switch is pressed on the operator interface 30. In step 505, the controller 35 checks if the viewing window 17 is locked by communicating with the viewing window lock 25. If the viewing window 17 is not locked, in step 510, a "close window" message is displayed in the operator interface 30. In step 515, the controller 35 waits up to 30 seconds for an operator to close the viewing window 17. The controller 35 then checks to see if the viewing window 17 is locked and if so, proceeds to step 520 where pump 40 is turned on by controller 35 to partially evacuate the cryostat chamber 19. In step 525, the controller waits approximately 60 seconds and samples the cryostat chamber 19 using sensor packet 55 that contains a pressure sensor to determine if a vacuum is still present in the chamber. In step 530, the controller 30 compares the stored vacuum level stored in step 520 with the sampled vacuum level obtained in step 525. If the two levels are not substantially equivalent, the controller 35 aborts the ozone generation process and displays an error message at the operator interface 30 at step 535.

If the stored vacuum level is equivalent to the sampled vacuum level, then in step 40 the controller 35 samples the ambient light level in the ozone generator 80. In step 545, the controller 35 illuminates an ultraviolet lamp. In step 550, the controller 35 compares the light level adjacent to the ultraviolet lamp with the ambient light level. If the light level has not increased above the ambient light level, then the controller aborts the ozone generating sequence and displays an error message at the operator interface 30. If the light level is greater than the sampled ambient light level, then in step 555 ozone is generated by the ozone generator 80. In one embodiment, the ozone generator 80 is located within the cryostat chamber 19. In an alternative embodiment, shown in FIGS. 2 and 4, the ozone generator 80 is located outside the cryostat chamber 19. With this embodiment, pump 40 pumps air from the cryostat chamber 19 through valve 70 that is instructed by controller 35 to direct air to the ozone generator 80 through tube 60. Ozone generated by passing air over the UV lamp in the ozone generator 80 is then directed through tube 60 into the cryostat chamber 19.

Figure 7:
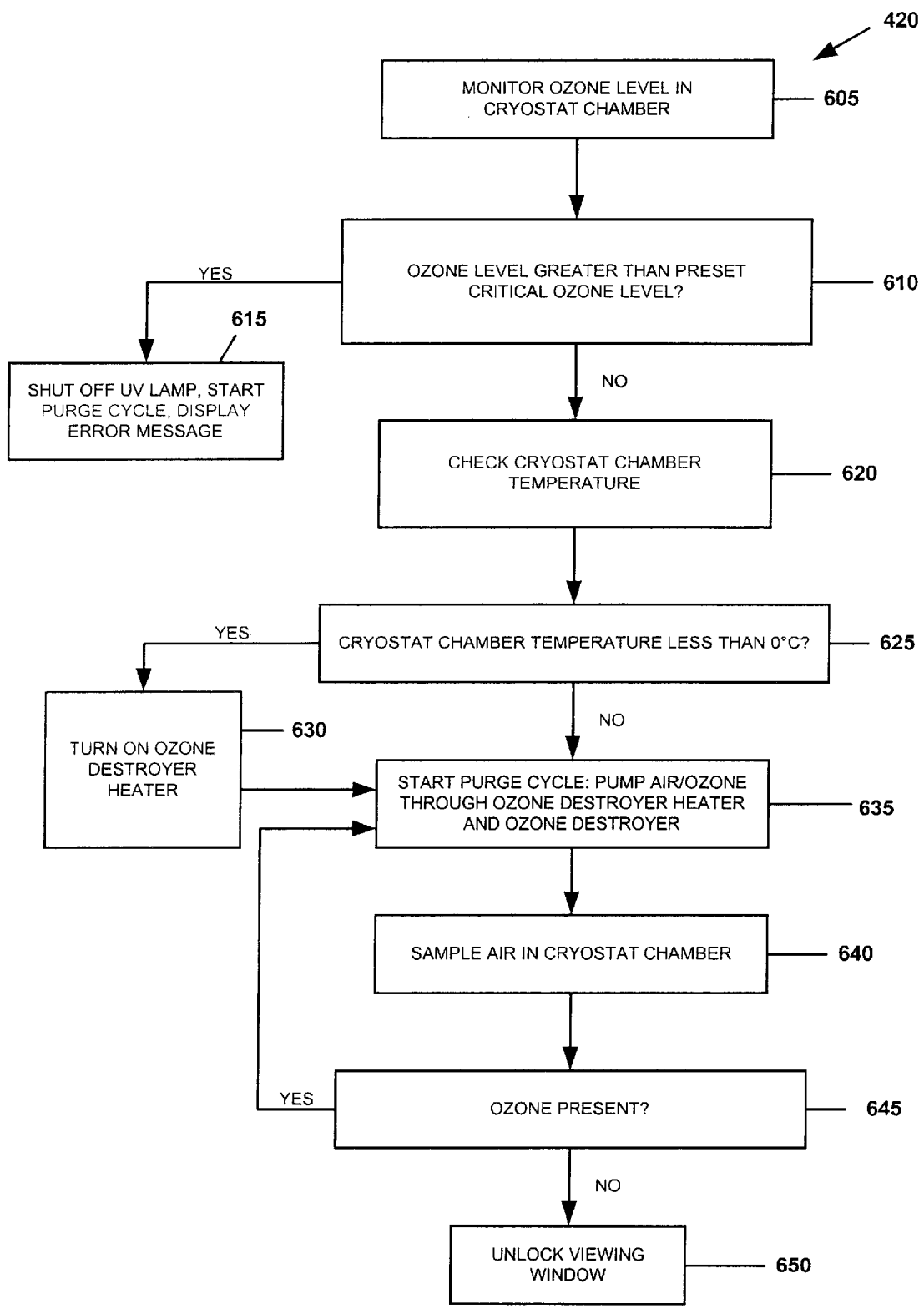
FIG. 7 is a flowchart illustrating one method of performing a method step shown in FIG. 5.

Referring to FIG. 7, the step 420 illustrated in FIG. 5 of destroying ozone is illustrated. In step 605, the controller 35 monitors the ozone level in the cryostat chamber 19. In step 610, the controller 35 samples the ozone level in the cryostat chamber 19 and compares it with a preset critical ozone level.

The preset critical ozone level may vary with the temperature of the cryostat chamber 19. Controller 35 obtains the cryostat chamber 19 temperature from a temperature sensor in sensor packet 55. The amount of ozone required to decontaminate the cryostat chamber 19 varies with the temperature of the cryostat chamber 19. When the chamber 19 is about +23 to +25 degrees Centigrade, an ozone concentration of about 250 parts per million is preferred. When the chamber 19 is about −30 degrees Centigrade, an ozone concentration of about 750 parts per million is preferred. However, the preferred ozone concentration may vary depending upon the amount of time allotted for decontamination. Therefore, the critical ozone level will also vary, but in one embodiment, the controller 35 will contain an algorithm that determines the appropriate critical ozone level.

In step 615, if the ozone level in the cryostat chamber 19 is equal to or greater than the critical ozone level, the controller 35 shuts off the UV lamp and starts the purge cycle and displays an error message on the operator interface 30. In step 620, if the ozone level is less than the critical level, the controller 35 checks the cryostat chamber temperature. In step 625, if the cryostat chamber temperature is less the 0° C., the controller 35 turns on the ozone destroyer heater in step 630. In step 635, if the cryostat chamber 19 temperature is greater than 0° C., then the purge cycle is started and pump 40 pumps the air and ozone present in the cryostat chamber 19 through the valve 70 and into the ozone destroyer heater and ozone destroyer 90. In one embodiment of present invention, air exiting the ozone destroyer 90 will be returned to the cryostat chamber 19. In another embodiment, air exiting the ozone destroyer 90 will be directed to the atmosphere.

In step 640, the controller 35 samples the air in the cryostat chamber 19. In step 645, if ozone is detected in the sampled air, the controller returns to step 635 and restarts the purge cycle. In step 650, if no ozone is present in the sampled air from the cryostat chamber 19, the controller 35 signals lock 25 to unlock the viewing window 17 and the ozone decontamination process is complete.

Thus, it is seen that an apparatus and method for sterilizing a microtome and cryostat are provided. One skilled in the art will appreciate that the present invention can be practiced by other than the preferred embodiments which are presented in this description for the purposes of illustration and not limitation and the present invention is limited only by the claims that follow. It is noted that the equivalents for the particular embodiments in this description may practice the invention as well.

What is claimed is:

1. A cryostat system comprising:
    an enclosable chamber;
    a pump communicating with the chamber;
    an ozone generator communicating with the chamber; and
    an ozone destroyer communicating with the chamber.

2. The cryostat of claim 1, further comprising a microtome located within the chamber.

3. The cryostat of claim 1, wherein the ozone destroyer communicates with the pump.

4. The cryostat of claim 1, wherein the ozone destroyer is selected from the group consisting of: a catalyst, a thermal ozone destroyer, carbon, activated carbon, a noble-metal catalyst, a manganese dioxide catalyst catalyst, and a CARULITE catalyst.

5. The cryostat of claim 1, wherein the pump removes a gas from the chamber and selectively directs the gas to the ozone generator and to the ozone destroyer.

6. The cryostat of claim 1, further comprising a valve coupled to the pump.

7. The cryostat of claim 6, wherein the valve is a three-way valve structured to be selectively manually and automatically operated.

8. The cryostat of claim 1, further comprising a second pump communicating with the chamber.

9. The cryostat of claim 8, wherein the second pump removes a gas from the chamber and selectively directs the gas back to the chamber and to the ozone destroyer.

10. The cryostat of claim 1, further comprising a filter.

11. The cryostat of claim 1, further comprising a heater.

12. The cryostat of claim 1, further comprising an ozone sensor.

13. The cryostat of claim 1, further comprising a temperature sensor.

14. The cryostat of claim 1, further comprising a pressure sensor.

15. The cryostat of claim 1, further comprising an electric power source structured to provide electric power to the cryostat.

16. The cryostat of claim 1, further comprising a locking member structured to secure a chamber door.

17. The cryostat of claim 1, wherein the ozone generator is selected from the group of consisting of: a lamp structured to produce ultraviolet radiation, and a corona discharge device.

18. The cryostat of claim 1 further comprising an operator interface structured to provide an interface between an operator and a controller.

19. The cryostat of claim 18, wherein the controller is a programmable general computing device structured to operate the pump, the ozone generator and the ozone destroyer.

20. The cryostat of claim 1, wherein the ozone generator is located within the cryostat chamber.

21. The cryostat of claim 1, wherein the ozone generator is located within the cryostat.

22. A method for decontaminating a cryostat, the method comprising the steps of:
    providing a cryostat chamber;
    introducing an ozone-containing gas into the cryostat chamber; and
    removing the ozone-containing gas from the cryostat chamber.

23. The method of claim 22, wherein the step of introducing the ozone-containing gas into the cryostat chamber comprises at least one of the steps of:
    producing the ozone-containing gas within the cryostat chamber; and
    producing the ozone-containing gas outside the cryostat chamber, and then directing the ozone-containing gas into the cryostat chamber.

24. The method of claim 22, further comprising the step of eliminating ozone from the ozone-containing gas after the ozone-containing gas is removed from the cryostat chamber.

25. The method of claim 24, wherein the step of eliminating ozone from the ozone-containing gas comprises directing the ozone-containing gas through a ozone destroying element.

26. The method of claim 25, wherein the ozone destroying element is selected from the group consisting of: a catalyst, a thermal ozone destroyer, carbon, activated carbon, a noble-metal catalyst, a manganese dioxide catalyst, and a CARULITE catalyst.

27. The method of claim 22, further comprising the step of securing the cryostat chamber prior to introducing the ozone-containing gas into the cryostat chamber.

28. The method of claim 22, further comprising the step of determining an integrity of the cryostat chamber.

29. The method of claim 28, wherein the step of determining the integrity of the cryostat chamber comprises the steps of:
    producing a partial vacuum pressure in the cryostat chamber;

storing the partial vacuum pressure;

waiting a predetermined time period;

sampling a pressure in the cryostat chamber; and comparing the partial vacuum pressure to the sampled pressure.

30. The method of claim 22, further comprising the step of determining an operation of an ozone generator.

31. The method of claim 30, wherein the step of determining an operation of an ozone generator comprises the steps of:

determining an ambient light level;

storing the ambient light level;

illuminating the ozone generator;

determining a light level adjacent to the ozone generator; and comparing the ambient light level to the light level adjacent to the ozone generator.

32. An apparatus for disinfecting a cryostat, comprising:

a cryostat chamber located in the cryostat;

means for introducing an ozone-containing gas into the cryostat chamber; and means for removing the ozone-containing gas from the cryostat chamber.

33. The apparatus of claim 32, wherein the means for introducing the ozone-containing gas into the cryostat chamber comprises at least one of:

means for producing the ozone-containing gas within the cryostat chamber; and means for producing the ozone-containing gas outside the cryostat chamber, and then means for directing the ozone-containing gas into the cryostat chamber.

34. The apparatus of claim 32, further comprising means for eliminating ozone from the ozone-containing gas after the ozone-containing gas is removed from the cryostat chamber.

35. The apparatus of claim 34, wherein the means for eliminating ozone from the ozone-containing gas comprises an ozone destroying element.

36. The apparatus of claim 32, further comprising means for securing the cryostat chamber prior to introducing the ozone-containing gas into the cryostat chamber.

37. The apparatus of claim 32, further comprising means for determining an integrity of the cryostat chamber.

38. The apparatus of claim 32, further comprising means for determining an operation of an ozone generator.

* * * * *

UNITED STATES PATENT AND TRADEMARK OFFICE
CERTIFICATE OF CORRECTION

PATENT NO.    : 6,481,219 B2
DATED         : November 19, 2002
INVENTOR(S)   : Henry William Palermo It is certified that error appears in the above-identified patent and that said Letters Patent is hereby corrected as shown below:

The title page showing the illustrative figures should be deleted to be replaced with the attached title page.

<u>Drawings,</u>
Sheets 1-4, consisting of Figs. 1 - 4, should be deleted to be replaced with the drawing sheets, consisting of Figs. 1 - 4, as shown on the attached pages.

United States Patent
Palermo

(10) Patent No.: US 6,481,219 B2
(45) Date of Patent: Nov. 19, 2002

(54) DISINFECTION SYSTEM AND METHOD OF USING SAME

(75) Inventor: Henry William Palermo, Burbank, CA (US)

(73) Assignee: Sakura Finetek U.S.A., Inc., Torrance, CA (US)

(*) Notice: Subject to any disclaimer, the term of this patent is extended or adjusted under 35 U.S.C. 154(b) by 0 days.

(21) Appl. No.: 09/822,150

(22) Filed: Mar. 30, 2001

(65) Prior Publication Data

US 2002/0139124 A1 Oct. 3, 2002

(51) Int. Cl.$^7$ .................................................. F25B 19/00
(52) U.S. Cl. ........................................................ 62/51.1
(58) Field of Search ......................................... 62/51.1, 78

(56) References Cited

U.S. PATENT DOCUMENTS

| | | | |
|---|---|---|---|
| 4,854,128 A | * 8/1989 | Zeamer | 62/50.1 |
| 5,156,019 A | 10/1992 | McCormick | |
| 5,255,585 A | 10/1993 | Gordon | |
| 5,452,584 A | 9/1995 | Diggs | |
| 5,520,893 A | 5/1996 | Kasting, Jr. et al. | |
| 5,624,734 A | 4/1997 | Rees et al. | |
| 5,628,197 A | 5/1997 | Rada | |
| 5,865,081 A | 2/1999 | Myers | |
| 5,914,089 A | 6/1999 | Murakami et al. | |
| 5,960,640 A | 10/1999 | Teppke | |
| 5,974,811 A | * 11/1999 | Heid et al. | 62/78 |
| 5,988,029 A | 11/1999 | Rotterman et al. | |
| 6,231,676 B1 | * 5/2001 | Rudd et al. | 134/1 |
| 6,280,633 B1 | * 8/2001 | Conrad et al. | 210/739 |

* cited by examiner

Primary Examiner—William C. Doerrler
Assistant Examiner—Malik N. Drake
(74) Attorney, Agent, or Firm—Luce, Forward, Hamilton & Scripps LLP

(57) ABSTRACT

An apparatus and method for disinfecting a microtome and cryostat is provided. The cryostat comprises a chamber, a pump communicating with the chamber, an ozone generator and an ozone destroyer. A microtome is located in the chamber. Oxygen molecules in ambient air are converted to ozone that is injected into the cryostat chamber, disinfecting the chamber and the microtome. After disinfection, the air and ozone present in the chamber is directed to an ozone destroying unit that eliminates any remaining ozone. This eliminates the risk of ozone exposure to nearby operators and minimizes damage to the cryostat and microtome from extended ozone contact.

38 Claims, 7 Drawing Sheets

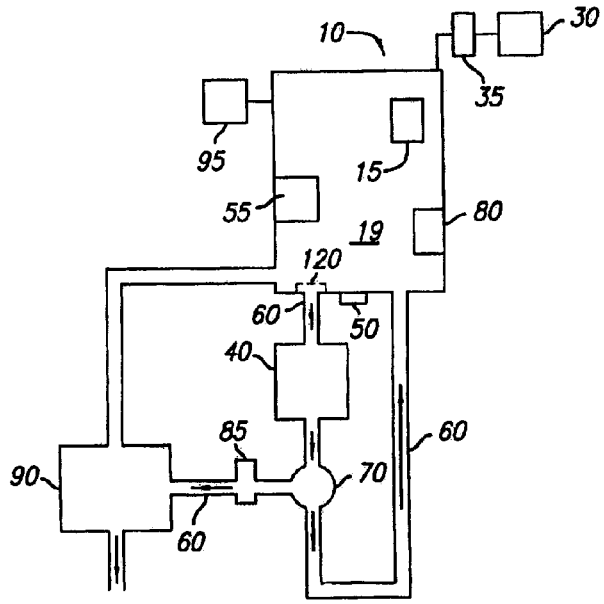

UNITED STATES PATENT AND TRADEMARK OFFICE
CERTIFICATE OF CORRECTION

PATENT NO.   : 6,481,219 B2
DATED        : November 19, 2002
INVENTOR(S)  : Henry William Palermo It is certified that error appears in the above-identified patent and that said Letters Patent is hereby corrected as shown below:

1 of 7

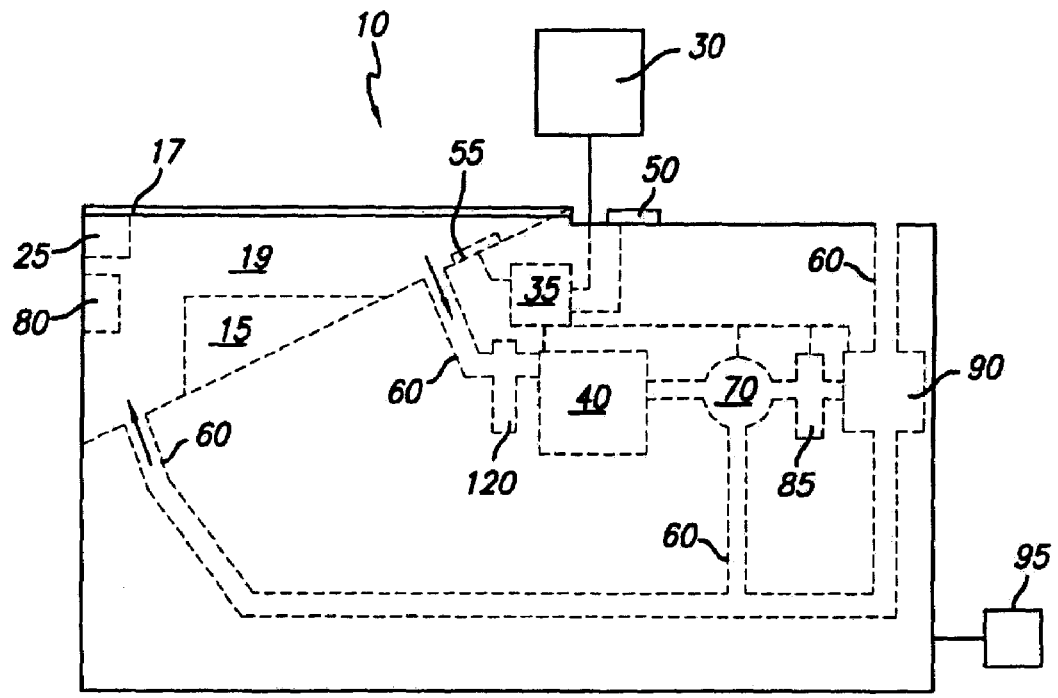

FIG. 1

UNITED STATES PATENT AND TRADEMARK OFFICE
CERTIFICATE OF CORRECTION

PATENT NO. : 6,481,219 B2
DATED : November 19, 2002
INVENTOR(S) : Henry William Palermo It is certified that error appears in the above-identified patent and that said Letters Patent is hereby corrected as shown below:

2 of 7

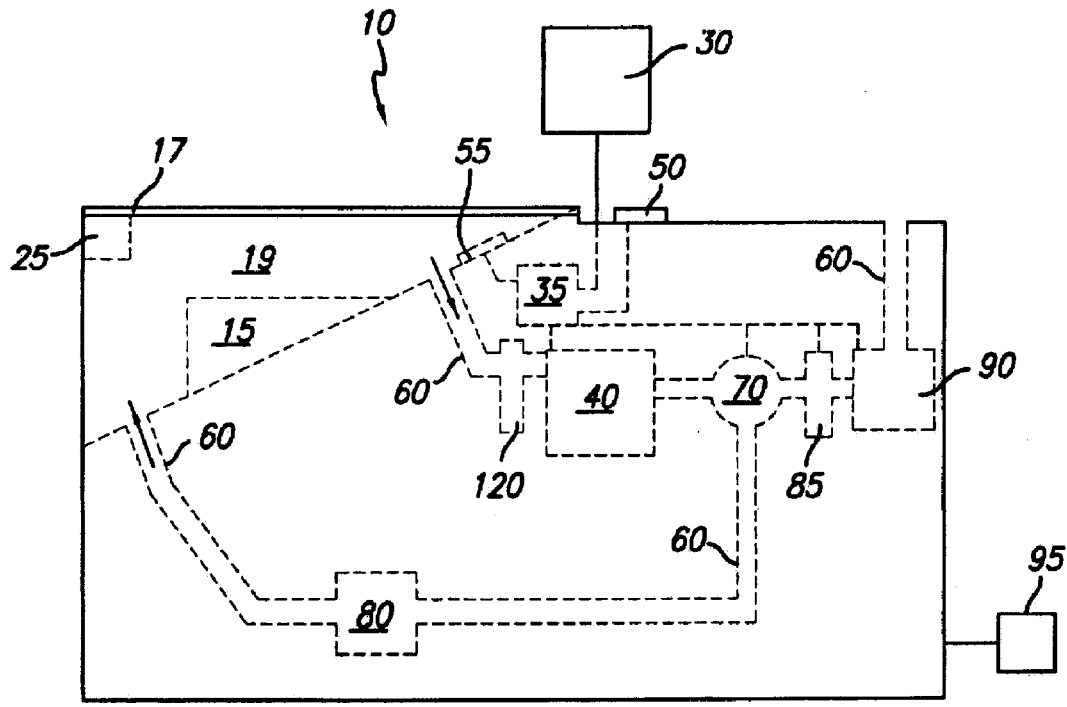

FIG. 2

UNITED STATES PATENT AND TRADEMARK OFFICE
CERTIFICATE OF CORRECTION

PATENT NO.    : 6,481,219 B2
DATED         : November 19, 2002
INVENTOR(S)   : Henry William Palermo It is certified that error appears in the above-identified patent and that said Letters Patent is hereby corrected as shown below:

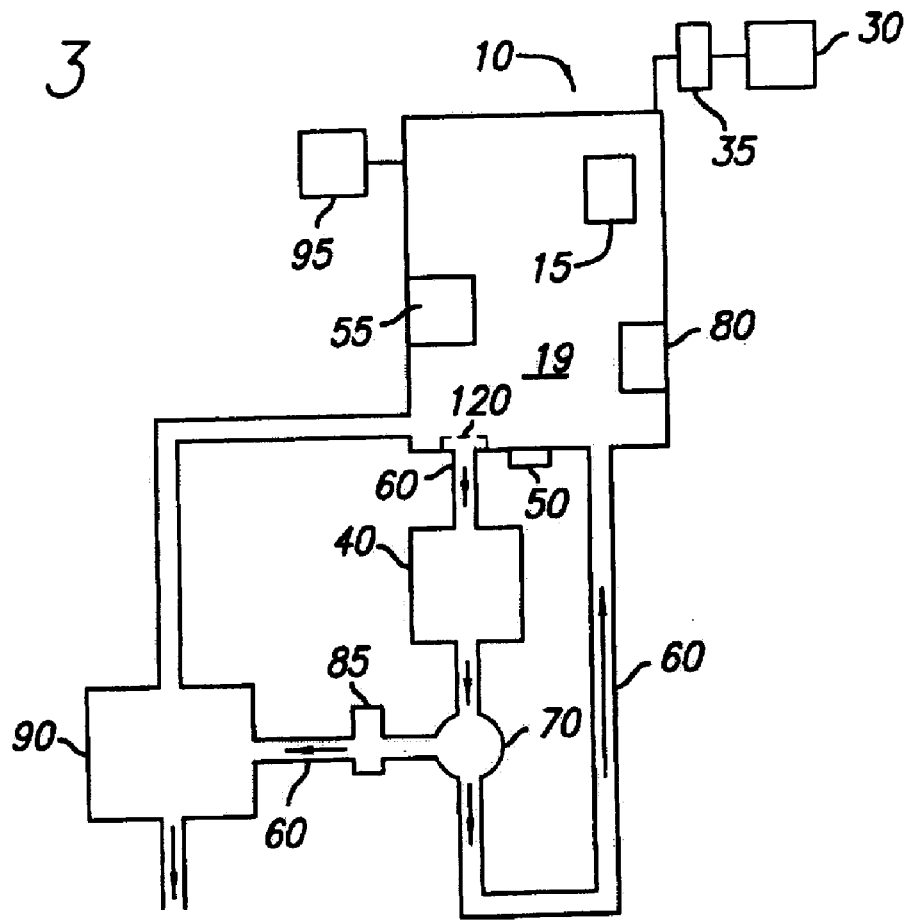

FIG. 3

UNITED STATES PATENT AND TRADEMARK OFFICE
CERTIFICATE OF CORRECTION

PATENT NO. : 6,481,219 B2
DATED : November 19, 2002
INVENTOR(S) : Henry William Palermo It is certified that error appears in the above-identified patent and that said Letters Patent is hereby corrected as shown below:

4 of 7

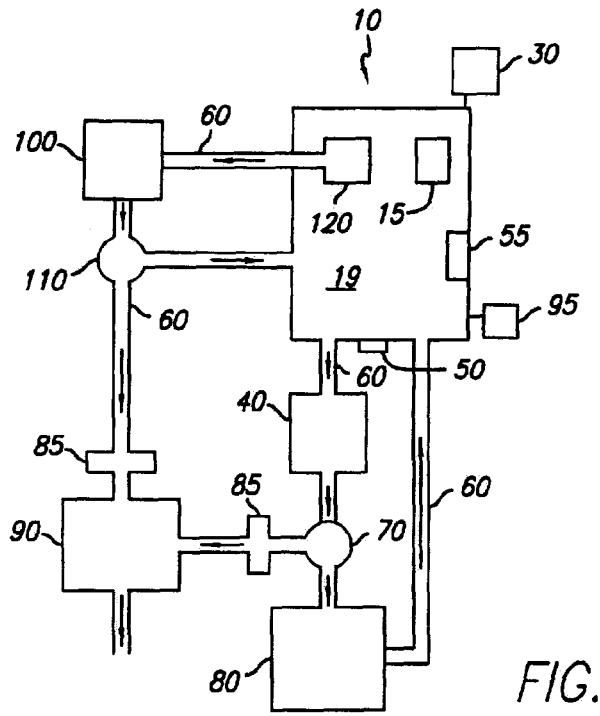

FIG. 4

Signed and Sealed this

Twenty-seventh Day of May, 2003

JAMES E. ROGAN
*Director of the United States Patent and Trademark Office*